United States Patent [19]
Tylor

[11] Patent Number: 5,117,059
[45] Date of Patent: May 26, 1992

[54] MONODISPERSE MULTIFUNCTIONAL CARBODIIMIDES

[75] Inventor: James W. Tylor, South Charleston, W. Va.

[73] Assignee: Union Carbide Chemicals & Plastics Technology Corporation, Danbury, Conn.

[21] Appl. No.: 645,094

[22] Filed: Jan. 24, 1991

Related U.S. Application Data

[63] Continuation-in-part of Ser. No. 360,108, Jun. 1, 1989, abandoned, which is a continuation-in-part of Ser. No. 1,833, Jan. 9, 1987, abandoned, which is a continuation-in-part of Ser. No. 747,190, Jun. 21, 1985, abandoned.

[51] Int. Cl.$^5$ .................. C08K 31/00; C07C 249/00
[52] U.S. Cl. ................................. 564/252; 524/832
[58] Field of Search .................. 564/252; 524/832

[56] References Cited

U.S. PATENT DOCUMENTS
4,977,219  12/1990  Watson, Jr. .................. 525/329.5

FOREIGN PATENT DOCUMENTS
924751  3/1981  Fed. Rep. of Germany .

Primary Examiner—Joseph L. Schofer
Assistant Examiner—Peter D. Mulcahy
Attorney, Agent, or Firm—Gerlad L. Coon

[57] ABSTRACT

Branched, monodisperse, multifunctional carbodiimides which are particularly useful as cross-linkers for carboxyl-containing resins.

24 Claims, No Drawings

MONODISPERSE MULTIFUNCTIONAL CARBODIIMIDES

This application is a continuation-in-part of application Ser. No. 360,108, filed Jun. 1, 1989, abandoned, which in turn is a continuation-in-part of application Ser. No. 001,833, filed Jan. 9, 1987, now abandoned, which in turn is a continuation-in-part of application Ser. No. 747,190, filed Jun. 21, 1985, now abandoned.

FIELD OF THE INVENTION

This invention relates to multifunctional, i.e., with more than two carbodiimide groups, monodisperse carbodiimides having particular structures, their preparation and use as cross-linking agents for carboxyl-containing organic resins, preferably latex resins, or neutralized, carboxylated water-soluble resins, and carboxylated solution resins.

SUMMARY OF THE PRIOR ART

Carbodiimides are a well-known class of organic compounds. Dicyclohexylcarbodiimide has been useful for many years as a condensation agent in the preparation of peptides, as described by Sheelan and Hess (J. Chem. Sol., 77, 1067 (1955)). Monodisperse, difunctional carbodiimide compounds have been prepared by the desulfurization of thioureas using hypochlorite. Such compounds were prepared, for example, by Iwakura, et al, (Makromol. Chem., 98, 21 (1966); Bull. Chem. Soc. Jpn., 40, 2383 (1967)). Multifunctional, linear, polydisperse polycarbodiimides have been prepared by Campbell from dicyanatoaklanes or dicyanatoarenes using a phospholine oxide catalyst (U.S. Pat. No. 2,941,966 (1960)). Use if sodium hypochlorite to desulfurize thioreas to multifunctional carbodiimides, i.e., with more than two carbodiimide groups, is reported to be very difficult (Wagner, et al, Angew. Chem., 70, 819 (1981)), and has previously not been successfully accomplished. No examples of linear, monodisperse carbodiimides with more than two carbodiimide units have been reported. While there are occasional gratuitous references in the literature to "branched" polycarbodiimides derived from the condensation of isocyanates, such systems are necessarily polydisperse in nature. Moreover, efforts to prepare such branched materials result in cross-linked gels which are not commercially useful. Examples of branched, monodisperse carbodiimides are unknown. The art is summarized in Chem. Rev., 81, 589 (1981).

The use of polydisperse polycarbodiimides as cross linkers for carboxylated latex resins and neutralized carboxylated water-soluble polymers is known in the art. Specifically, co-assigned U.S. application Ser. No. 691,378, filed Jan. 15, 1985 (the disclosure of which is incorporated herein by reference), teaches the preparation of useful polycarbodiimide crosslinkers from certain mono-, di-, and tri-functional cycloaliphatic or saturated aliphatic isocyanates, in which the mono- and diisocyanates are optional. Co-assigned U.S. Pat. No. 4,487,964 discloses the preparation of useful polycarbodiimide crosslinkers from mixed aromatic/aliphatic isocyanates. In both instances, the polycarbodiimides produced inherently contain a broad range of molecular weights, i.e., are polydisperse. While such polycarbodiimides have general utility as crosslinkers, their polydisperse nature makes them less than satisfactory in many uses and limits their overall efficiency as crosslinking agents.

SUMMARY OF THE INVENTION

The present invention provides improvements over the prior art in several important respects. Now, for the first time, there are presented, in monodisperse form, branched tri- and higher multifunctional polycarbodiimides. These compounds are not only particularly effective as crosslinking agents, they also provide exact functionality, i.e., a pre-designed, branched structure with a known degree of functionality and a single molecular weight. Because of this latter fact, these multifunctional carbodiimides are, for the first time, monodisperse, with the advantages attendant to reactive systems made from such materials, as will be apparent from the disclosure herein. For example, monodisperse systems will not contain undesired molecular weight fragments, and will provide better accessibility of all functional groups and greater reaction efficiency at lower temperatures.

In one aspect of the present invention, there is provided a branched, monodisperse, multifunctional carbodiimide conforming to the generalized structure:

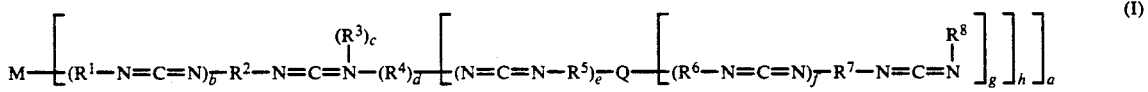

(I)

wherein:
M and Q are independently the residue of a compound adapted to function as a site for branching; $R^1$, $R^2$, $R^4$, $R^5$, $R^6$ and $R^7$ are independently divalent organic radicals; $R^3$ and $R^8$ are independently monovalent organic radicals;

a is an integer having a value from 3 to about 6 corresponding to the valence of M;

b is an integer having a value from 0 to about 4;

c is an integer having a value of 0 or 1;

d is an integer having a value of 0 or 1;

e is an integer having a value of from 0 to about 4;

f is an integer having a value of from 0 to about 4;

g is an integer having a value of from 0 to about 4;

h is an integer having a value of 0 or 1, wherein for each value of a, $R^1$, $R^2$, $R^3$, $R^4$, $R^5$, $R^6$, $R^7$, $R^8$, b, c, d, e, f, g and h may be the same or different, with the provisos that:

(i) for each a, the sum of c +d is 1;

(ii) for each a wherein d is 0, e, f, g, and h all have a value of 0; and (iii) for each a wherein d is 1 and h is 1.

As represented by Formula I, $R^1$, $R^2$, $R^4$, $R^5$, $R^6$ and $R^7$ are independently substituted or unsubstituted alkyl (including cycloalkyl) or aryl radicals, wherein such substituted alkyl and aryl radicals include radicals having substituents selected from the group consisting of cyano, nitro, halo, alkylthio, dialkylaminoalkyl, alkylsilyl, alkoxy, and aryloxy moieties, and the like. As represented by Formula I, $R^3$ and $R^8$ are independently substituted or unsubstituted alkylene or arylene radicals, wherein such substituted alkylene and arylene radicals include radicals having substituents selected from the group consisting of cyano, nitro, halo. alkylthio, dialkylaminoalkyl, alkylsilyl, alkoxy, and aryloxy moieties, and the like.

More specifically, there is provided a monodisperse, branched, multifunctional carbodiimide conforming to the structure:

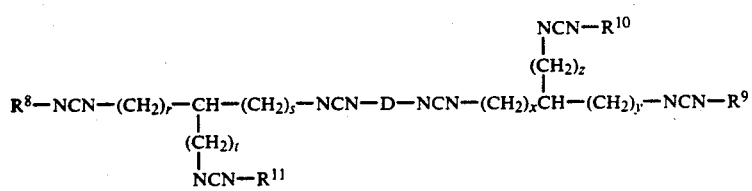

wherein: $R^8$, $R^9$, $R^{10}$, $R^{11}$ may be the same or different and represent organic residues which do not substantially interfere with the multifunctional carbodiimide for its intended purpose; and D is an organic residue.

Still more specifically, there is provided a monodisperse, branched, multifunctional carbodiimide conforming to the structure:

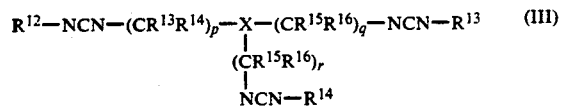

wherein: $R^{12}$, $R^{13}$, and $R^{14}$ may be the same or different and represent alkyl groups having 1 to about 12 carbon atoms; $R^{15}$ and $R^{16}$ may be the same or different and represent hydrogen, alkyl (including cycloalkyl), aryl, aralyl, alkaryl, heterocyclic, cyano, nitro, halo, alkyl thio, dialkylaminoalkyl, silyl, alkoxy, and aryloxy groups, and substituted species of any of the foregoing; X is the residue of a compound adapted to function as a site for branching; p, q and r may be the same or different and represent integers from 0 to about 12.

Particularly desirable monodisperse, branched, multifunctional carbodiimides are those of the formula:

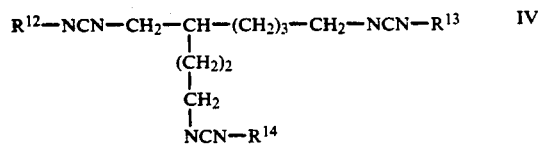

wherein $R^{12}$, $R^{13}$ and $R^{14}$ are aromatic groups; cycloaliphatic groups or alkyl groups having 1 to 6 carbon atoms.

Carbodiimides, as defined, having methyl, isopropyl, n-butyl, cyclohexyl or phenyl end groups are especially desirable as they serve as particularly efficient crosslinking agents at relatively low temperatures, as shown by the data of Table III of this specification.

There are also provided cross-linkable compositions comprising a mixture of a carboxyl-containing emulsion resin, e.g., latex, or neutralized, carboxylated water-soluble organic resin, e.g., a latex at least partially neutralized, or carboxylated solution resin, with such multifunctional carbodiimides.

In addition, there is provided a method for crosslinking such resins comprising mixing same with ~0.5 to ~15, preferably ~1 to ~7, parts per hundred parts by weight of such resin ("PHR") of a branched, monodisperse, multifunctional carbodiimide in emulsified or water solution form and allowing volatilization of certain formulated materials, resulting in a crosslinked product.

Moreover, this invention provides a method for crosslinking a carboxylated solution resin, comprising mixing same with ~0.5 to ~15, preferably ~1 to ~7, parts per hundred parts by weight of such resin of a branched, monodisperse multifunctional carbodiimide in an organic solvent, and removing the solvent.

Finally, this invention provides, as new compositions of matter, the multifunctional amines, multifunctional ureas and multifunctional thioureas which are the precursors for the above-described monodisperse, branched, multifunctional carbodiimides.

As used herein, all defined groups are intended to include such groups containing any substitution which does not significantly interfere with the use of the multifunctional carbodiimides as crosslinking agents. Likewise, all aromatic groups are intended to include fused aromatic rings as well as substituted aromatic groups.

As used herein, the terms "multifunctional" and "polyfunctional" are interchangeable and signify three or more of the same functional group (e.g. carbodiimide), as distinguished from "polycarbodiimide," as in the prior art, which connotes polydispersity and which may also signify polymeric carbodiimides which may have differing functional groups.

DETAILED DESCRIPTION OF THE INVENTION

This invention discloses as new compositions of matter, monodisperse, branched, multifunctional carbodiimides, as well as the branched ureas or thioreas from which such multifunctional carbodiimides may be made. These materials are produced with exact, predetermined functionality, and thus are particularly effective, reproducible and predictable in performance. The multifunctional carbodiimides of this invention have the additional advantages of being surprisingly low in viscosity for their molecular weight, and can be readily converted to water-soluble versions or monodisperse emulsions using equipment and procedures commonly available in the art.

The term "polydisperse" is used herein in its well understood sense of referring to systems having a molecular weight distribution. Such systems are reflected by the well-known equation:

$$\text{Polydispersity Index} = \frac{M_w}{M_n} > 1.$$

Conversely, in the "monodisperse" systems of this invention, $M_w = M_n$ and the Polydispersity Index $= 1$, i.e., there is no molecular weight distribution. (It will be understood, of course, that if polydispersity is present in the carbodiimide precursors, it will also confer some degree of polydispersity on the polycarbodiimide. Accordingly, therefore, the precursors are desirably prepared as free from polydispersity as possible, e.g., over about 95% purity.)

Whereas all commercially useful polycarbodiimides of the prior art are linear in structure, that is, all carbodiimide groups are along the same "line of sight" (i.e., along the same polymer chain), the instant multifunctional carbodiimides are branched (sometimes referred to as "star") structures. (The term "branched," as used herein and as embodied in Formulas I, II, III and IV above, is intended to include not only relatively simple star structures such as 1,3,6-tri-(N-alkyl-N'-methylene carbodiimide)hexane, but also more complex structures wherein the branches may be spaced out along a backbone chain, which may itself contain one or more carbodiimide linkages).

The moieties designated M, Q, D, and X in the above formulas are intended to be quite broad and general in scope. It will be readily appreciated from these formulas that by careful choice of starting materials and reaction sequence, all within the scope of this invention, it will be possible to prepare complex molecular structures. All such monodisperse structures will be new in the art, and should share the advantages indicated above. Accordingly, it is to be understood that M, Q, D, and X are intended to include all structures which do not significantly impair the use of the branched multifunctional carbodiimides for their intended purpose.

A significant shortcoming of the polycarbodiimides of the prior art is that their polydisperse nature limits their efficiency as crosslinking agents. Without intending to be bound by any particular theory, it is believed that the lower molecular weight fractions of the polydisperse products are not particularly effective as crosslinkers, while the higher molecular weight fractions are slow to diffuse into the crosslinkable resin particles at the relatively low temperatures desired for so-called "low bake" coating systems. The multifunctional carbodiimides of the instant invention are believed to solve this problem by providing a relatively high degree of carbodiimide functionality at relatively low molecular weight. Moreover, the branched structure is believed to provide more efficient accessibility of carbodiimide groups to reactive sites on the crosslinkable resin particles than is the case when the carbodiimide groups are aligned along a single polymer chain.

Selection of optimum molecular weight will be a matter of experimentally balancing, for example, such variables as the degree of branching, the distance between carbodiimide moieties, backbone chain length, and the compatibility of the polycarbodiimide with the crosslinkable resin. As a general guideline, referring to Formulas, I, II and III, the ranges for the subscript letters are:

a=3 to ~6, preferably 3;
b=0 to ~4, preferably 0 or ~1;
c=0 or ~1, preferably 1;
d=0 or ~1, preferably 1;
e=0 or ~4, preferably 0;
f=0 or ~4; preferably 0;
g=0 to ~4, preferably 0;
h=0 to ~1, preferably 0;
p=0 to ~12, preferably 1 to ~2;
q=0 to ~12, preferably 3 to ~4;
r=0 to ~12, preferably 2 to ~3;
s=1 to ~6, preferably 1 to ~4;
t=1 to ~6, preferably 1 to ~4;
x=1 to ~6, preferably 1 to ~4;
y=1 to ~6, preferably 1 to ~4;
z=1 to ~6, preferably 1 to ~4;

The above tabulation is offered with the observations that a must be at least 3 for branching to occur.

While the branched, monodisperse, multifunctional carbodiimide structures of this invention may theoretically be derived through various chemical reactions, as a practical matter, it is believed that it is most expeditious to prepare them by the known technique of conversion of a suitable polyfunctional amine to a urea or thiourea, and the dehydration or desulfurization of these to the corresponding polyfunctional carbodiimide. For example, 1,3,6-tri(N-alkyl-N'-methylene carbodiimide)hexane, a preferred compound of this invention, may be prepared from the triamine 4-(aminomethyl)-1,8-diaminooctane:

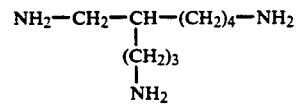

available from Oxid, Inc., Houston, Tex. While the conversion procedures will be more explicitly demonstrated in the examples below, the reaction may be described in general terms as follows:

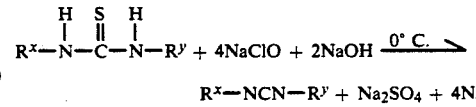

wherein the exact nature of $R^X$ and $R^Y$ is not of importance for purposes of the illustration.

While this route has the advantage of relative simplicity, it suffers from the shortcoming of producing sulfur and sulfur compounds as by-products. While these are not believed to interfere substantially with the effectiveness of the polyfunctional carbodiimides as crosslinkers, removal of odorous sulfur components may be desirable for some applications.

An alternative, although more complex procedure, involves reaction of a polyfunctional amine with, e.g., cyclohexyl isocyanate in the presence of bromotriphenyl phosphine bromide. This route produces the multifunctional carbodiimide in good purity; however, triphenyl phosphene oxide is produced as a waste product. The general reaction for this route to polyfunctional carbodiimides is as follows:

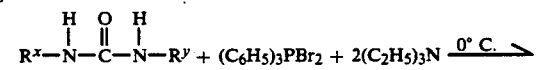

wherein $R^X$ and $R^Y$ are as above.

Referring again to Formulas II and III, the groups designated $R^8$, $R^9$, $R^{10}$, $R^{11}$, $R^{12}$, $R^{13}$, $R^{14}$ and either $R^{15}$ or $R^{16}$ may be any monovalent aliphatic or aromatic radical which does not substantially interfere with the utility of the polyfunctional carbodiimide for its intended purpose. The aliphatic radicals, which may be substituted, are normal, branched, or cycloalkyl, preferably containing from 1 to 12 carbon atoms, and alkenyl. Thus, for example, the aliphatic radicals which may be employed as substituents are: methyl, ethyl, n-propyl, isopropyl, n-butyl, sec.-butyl, isobutyl, tert.-butyl, amyl, isohexyl, heptyl, n-octyl, tert.-octyl, nonyl, decyl, undecyl, n-dodecyl, cyclohexyl, methoxymethyl, ethoxymethyl, carbethoxy, methoxyethyl, ethoxy, propoxy, diethylaminoethyl, β-diethylaminoethyl, dimethylaminopropyl, diethylaminopropyl, diethylaminocyclohexyl, 2-morpholinyl-(4)-ethyl, α- and β-phenyl ethyl, benzyl, 1-methyl bornyl, trityl, benzoyl, allyl, 2-bromoalkyl and crotyl. Useful aromatic radicals, which may also be substituted, include phenyl, p- and m-fluorophenyl, p- and m-chlorophenyl, p- and m-bromophenyl, p- and m-iodophenyl, 2,4-difluorophenyl, 2,4-dichlorophenyl, 2,4-dibromophenyl, 2,4-diiodophenyl, p- and m-methoxylphenyl, p-isobutylphenyl, p-propylphenyl, p- and o-carbethoxyphenyl, p-diethylaminophenyl, m-acetylphenyl, p-, o-, and m-tolyl, and α- and β-naphthyl. It is obvious from the foregoing that the substituent R-groups in the above formulas may be normal, branched and cycloalkyl containing 1 to 12 carbon atoms, alkenyl, or aryl. The alkyl may be substituted with, e.g., halogen, lower alkyl, lower alkoxy, di-lower alkyl amino, morpholine and mono-aryl-substituted lower alkyl substituents. The alkenyl may have, e.g., halogen substituents. The aryl radical may have, e.g., halogen, cyano, nitro, acetyl, lower alkyl, lower alkoxy and di-lower alkyl amino substituents. The R-radicals may be the same or different.

In the event that it is desired to produce water-soluble polyfunctional carbodiimides, it is desirable to utilize such substituents as diethylaminoethyl, β-diethylaminoethyl, dimethylaminopropyl, diethylaminopropyl, diethylaminocyclohexyl, and the like, as well as alkoxy and aryloxy groups.

As has been mentioned, it is a particular advantage of the polyfunctional carbodiimides of this invention that they have a relatively low viscosity at any given molecular weight. Viscosity will, of course, be adjustable by addition of solvent. It has been found that typical viscosities for the multifunctional carbodiimides in the Examples below range from ~14 to ~160 cps at ~94% solids in hexane. Viscosities at 100% solids have not been determined since temperatures required to drive off the residual solvent would tend to cause polymerization of the polyfunctional carbodiimide. For most formulation work, the presence of a few percent solvent in the polyfunctional carbodiimide is inconsequential. Since ~1,000 cps is probably a practical maximum for latex formulating work, it is apparent that the instant polyfunctional carbodiimides have a very desirable viscosity level for commercial utility.

The multifunctional carbodiimides made according to this invention are to be converted into a form which is useable in water-borne systems. In this step, for example, a multifunctional carbodiimide solution, water, and optional ingredients such as surfactants and stabilizers are mixed to yield an emulsion. In a typical preparation, about 32 parts of a water solution which contains about 0.8% CELLOSIZE QP-52000, 2% triethylamine, 1.5% TERGITOL NP-40, and 2% Aerosol-OT, is added to about 40 parts of a stirred multifunctional carbodiimide solution which is about 47% active carbodiimide in an organic solvent such as amyl acetate. The resultant material thus appears as a low viscosity, opaque liquid with the multifunctional carbodiimide dispersed in the continuous phase. If desired, the emulsion may be homogenized in a high-shear environment by an apparatus such as a Virtis or Manton-Gaulin homogenizer. A volatile amine is sometimes employed to ensure that the pH of the emulsion is maintained adequately high. Exemplary volatile amines include triethylamine, dimethylethanolamine, dimethylamine, diethylamine, and the like, including ammonia. It is desirable that the pH of the carbodiimide emulsion be above ~8, preferably ~8 to ~10, most preferably ~8 to ~8.5, to enhance stability, i.e., to impede hydrolysis of the carbodiimide groups.

The types and concentrations of the emulsion components may vary widely, as will be recognized by those skilled in the art. For example, the levels of the reactant multifunctional carbodiimide and stabilizer may be widely varied, as may the type of surfactant employed. The nature of the surfactant system may have a strong influence on the degree, type, and time of system mixing required. It may also be desirable to employ a co-solvent for one or more formulation ingredients, with the proviso, however, that such co-solvent should have little or no water solubility.

As previously indicated, the polyfunctional carbodiimides of this invention are effective crosslinking agents for emulsion resins, and the like, in aqueous medium. The key requirement of the crosslinkable formulation is that the latex or emulsion polymer, or semi-solubilized colloidal polymer, or solution polymer in water, contains carboxylic acid functionality. Many systems contain the carboxylic acid functionality from copolymerization of acids, such as acrylic acid, methacrylic acid, or itaconic acid. Alternatively, maleic, fumaric or crotonic acid may be employed as co-monomers. The level of acid in commercially available polymers is extremely variable, e.g., from about 1% to about 40% by weight; however, the 2% to 5% region is estimated to be most preferred.

It is known that the reaction rate between carboxyl groups and carbodiimide groups is pH-dependent; that is, neutralized carboxyl groups react relatively slowly, while unneutralized carboxyl groups react relatively rapidly. Accordingly, in order to enhance the stability of the fully-formulated compositions, it is desirable to control pH. It is recommended that the pH of the fully-formulated compositions be adjusted. If necessary, to the range of about 3 to about 10, preferably about 6.5 about 9. This may be readily accomplished by addition of a volatile amine, preferably an alkanolamine, e.g., triethanolamine or dimethylethanolamine. As the volatile amine leaves the coating, neutralized carboxy groups are freed for rapid reaction with carbodiimide groups.

It has also been indicated that the polyfunctional carbodiimides of this invention are effective crosslinking agents for carboxyl-containing resins in organic solution form. For such use, it is desirable that the polyfunctional carbodiimide be present as a "solution" in a solvent miscible with that containing the crosslinkable resin. It is to be noted that, in solution form, the reaction proceeds very rapidly, which could result in premature gellation. It is desirable, therefore, that the mixing of the two solutions be accomplished at or immediately prior to application to the substrate to be coated with the crosslinkable resin. This may be accomplished by use of physical devices familiar to the art, e.g., the mixing heads commonly used for mixing two-part, isocyanate-curing, coating systems. Alternatively, the two solutions could be separately applied and allowed to mix on the surface of the substrate.

While the basic ingredients of the crosslinked coatings are the carboxylated polymer and the monodisperse, branched multifunctional carbodiimide crosslinker, it is obvious that many additional ingredients may be present to serve useful roles for special applications. For example, pigments, fillers and colorants may be used to provide hiding power and decorative effects. Water-soluble polymers may be employed for control of coating rheology, while dispersants and foaming or defoaming agents may be required in particular applications. Such functional additives are known to the art, and their use may ordinarily be determined by routine experimentation.

EXAMPLES

The examples which follow illustrate but are in no way intended to limit the invention.

| Glossary of Materials Used | |
|---|---|
| AEROSOL-OT | Trademark of American Cyanamid Co. for the sodium salt of dialkyl sulfosuccinate (used as a surfactant) |
| Butyl CELLO-SOLVE | Trademark of Union Carbide Corporation for a monoalkyl ether of ethylene glycol |
| CARBOWAX (Methoxy-polyethylene glycol | Trademark of Union Carbide Corporation for hydroxy terminated poly(ethylene glycols) |
| CELLOSIZE QP-52,000 | Trademark of Union Carbide Corporation for an ethoxylated cellulose (used as a stabilizer) |
| TERGITOL NP-40 | Trademark of Union Carbide Corporation for an ethoxylated alkyl phenol (used as a surfactant) |
| UCAR Latex 4431 | Trademark of Union Carbide Corporation for a carboxylated emulsion polymer |
| UCAR Latex 4620 | Trademark of Union Carbide Corporation for a carboxylated emulsion polymer |
| XAMA-7 | Trademark of Cordova Corporation for a water-soluble, polyfunctional aziridine crosslinker commercially used for carboxylated polymers |
| Leneta Paper | A commonly used, heavy-gauge paper to which test coatings are applied. Made by Leneta Paper Company |
| Test and Terms | |
| Double-Rub Test | A piece of cheesecloth is saturated with methyl ethyl ketone, then rubbed on the substrate until the coating is penetrated. One back-and-forth rub is a double-rub. |
| PHR | Parts of dry crosslinker resin used in an aqueous formulation per 100 parts of dry polymer resin. |

In the following examples, all parts and percentages are by weight unless otherwise specified. The following groupings of the data may be of interest.

Examples 1, 7, 9, 10 and 12 show the conversion of a commercially available triamine to corresponding ureas and thioureas.

Examples 2-6 show the preparation of a variety of 1,3,6-tri(N-alkyl(or aryl)-N'-methylene carbodiimide) hexanes using ureas as starting materials.

Examples 8, 11 and 13 show the preparation of a variety of 1,3,6-tri(N-alkyl-N'-methylene carbodiimide) hexanes using thioureas as starting materials.

Examples 16-19 show the crosslinking ability of the 1,3,6-tri(N-alkyl(or aryl)-N'-methylene carbodiimide) hexanes in carboxylated resins.

Example 20 addresses stability considerations.

EXAMPLE 1

Preparation of 1,3,6-tri(N-isopropyl-N'-methylene urea) hexane

Into a 3-neck, 2,000 ml, round-bottom flask equipped with a condenser, mechanical stirrer, thermometer, and dropping funnel were charged 150.0 g (1.762 moles) of isopropyl isocyanate and 900 ml of methylene chloride. The contents of the reactor were cooled to 2° C., then 101.84 g (0.5874 mole) of 4-aminomethyl-1,8-octane diamine (purified to approximately 98% purity by distillation) in 75.2 ml of methylene chloride were added to the stirred methylene chloride solution of isopropyl isocyanate at such a rate as to keep the temperature less then 33° C. After the feed, the dropping funnel was rinsed through with 50 ml of methylene chloride. The contents of the flask were then heated at 37° C. for 30 minutes. After the reaction, the swollen tri-functional urea was removed, then dried under vacuum at 64° C. to remove residual methylene chloride.

The infrared spectrum of the white powder, in a potassium bromide pellet, showed a large carbonyl band at 1,630 cm$^{-1}$ and an amide band at 1,565 cm$^{-1}$, which is characteristic of an unsymmetrical dialkylurea. The yield of product was 95.3%.

This urea was used to prepare the 1,3,6-tri(N-isopropyl-N'-methylene carbodiimide) hexane described in Example 2. The general procedure of Example 1 was also used to prepare the ureas used to Examples 3-6.

EXAMPLE 2

Preparation of 1,3,6-tri(N-isopropyl-N'-methylene carbodiimide)hexane

Into a 3-neck, 5,000 ml, round-bottom flask equipped with a thermometer, mechanical stirrer, and pressure-equalizing dropping funnel were charged 484.59 g (1.847 moles) of triphenylphosphine and 2585 ml of dried methylene chloride. The contents of the flask were cooled to 1° C., then 295.2 g (1.847 moles) of bromine dissolved in 200 ml of methylene chloride were dropped into the stirred triphenylphosphine solution over a 1.73-hour period while maintaining the temperature of the contents of the flask between 1° and 6° C. After the addition of the bromine solution, 377.7 g (3.733 moles) of triethylamine were added to the bromotriphenylphospine bromide solution over a 1.3-hour period while maintaining the temperature between 0° and 1° C.

To prepare the multifunctional carbodiimide, 220.0 g (0.5132 mole) of 1,3,6-tri(N-isopropyl-N'-methylene urea) hexane were added portionwise to the stirred solution of bromotriphenylphosphine bromide solution over a 1-hour period while maintaining the temperature of the contents in the flask between 0° and 2° C. After the addition of the urea, the contents of the flask were stirred for 1.75 hours.

After the reaction period, triphenylphosphine oxide and triethyl hydrogen bromide were filtered from the methylene chloride solution containing the carbodiimide. The solution containing the multifunctional carbodiimide was then washed with 4175 g of cold water. The polycarbodiimide solution was then dried overnight over 4Å molecular sieves.

The methylene chloride was then removed using a roto-evaporator at 38° C. (345 mm Hg). The vacuum was gradually increased to 5 mm Hg. The 1,3,6-tri(N-isopropyl-N'-methylene carbodiimide) hexane was then extracted from the triphenylphosphine oxide residue with four 1,400 ml portions of hexane. The extracts were filtered, then combined to form a clear solution of the multifunctional carbodiimide in hexane. The hexane was removed using a roto-evaporator at 38° C. (115 mm Hg) until 350 ml of solution remained. The solution was refiltered, and most of the remaining hexane removed using a roto-evaporator at 38° C. (7 mm Hg).

The infrared spectrum of clear amber oil showed a larger carbodiimide band (2130 cm$^{-1}$). The carbodiimide solution, which was 94.2% active in hexane, had a Brookfield viscosity of 14 cps (LVT #1 spindle at 60 rpm). The equivalent Gardner Bubble viscosity was 0.144 Stoke. The yield of the carbodiimide was 80.3%. Titration of an aliquot by the procedure of Zarembo and Watts (*Microchem. J. Symp. Ser.*, 2, 591 (1962) yielded a carbodiimide functionality of 26.8% (theory 32.0%). The theoretical functionality of the material was 3.

EXAMPLE 3

Preparation of 1,3,6-tri(N-tert.-butyl-N'-methylene carbodiimide) hexane

Into a 3-neck, 2,000 ml. round-bottom flask equipped with a thermometer, mechanical stirrer, and pressure-equalizing dropping funnel were charged 200.57 g (0.7647 mole) of triphenylphosphine and 1030.7 ml of dried methylene chloride. The contents of the flask were cooled to 1° C. then 122.21 g (0.7647 mole) of bromine in 122 ml of methylene chloride were dropped slowly into the stirred triphenylphosphine solution over a 1.4-hour period while maintaining the temperature of the contents of the flask between 1° and 10° C. After addition of the bromine solution, 156.69 g (1.5455 moles) of triethylamine were added to the bromotriphenylphosphine bromide solution over a 40-minute period while maintaining the temperature between 1° and 4° C.

To prepare the multifunctional carbodiimide, 100.0 g (0.2124 mole) of 1,3,6-tri(N-tert.-butyl-N'-methylene urea) hexane were added portionwise to the stirred solution of bromotriphenylphosphine bromide solution over about a 1-hour period while maintaining the temperature between 1° and 35° C. After the addition of the urea, the contents of the flask were stirred for 2 hours.

After the reaction period, the triphenylphospine oxide and triethylhydrogen bromide were filtered from the methylene chloride solution containing the carbodiimide, and the methylene chloride solution washed with 1728 g of cold water. The methylene chloride solution was then dried overnight over 4Å molecular sieves.

The methylene chloride was then removed using a roto-evaporator at 38° C. (348 mm Hg). The 1,3,6-tri(N-tert.-butyl-N'-methylene carbodiimide) hexane was then extracted from the triphenylphosphine oxide residue with four 580 ml portions of hexane. The extracts were filtered and combined to form a clear solution. The hexane was removed using a roto-evaporator at 38° C. (112 mm Hg) until about 120 ml of solution remained. The solution was refiltered, and most of the remaining hexane removed in a roto-evaporator at 39° C. (5 mm Hg).

The infrared spectrum of the clear amber oil showed a large carbodiimide band (21130 cm$^{-1}$). The multifunctional carbodiimide solution, which was 93.9% active in hexane, had a Brookfield viscosity of 160 cps (LVT #1 spindle at 30 rpm). The yield of multifunctional carbodiimide was 61.6%. Titration of an aliquot by the procedure of Zarembo and Watts yielded a carbodiimide functionality of 21.5% (theory 28.8%). The theoretical functionality of the material was 3.

EXAMPLE 4

Preparation of 1,3,6-tri(N-n-butyl-N'-methylene carbodiimide) hexane

The preparation of the polyfunctional carbodiimide was as described in Example 3 except that 100.0 g (0.2124 mole) of 1,3,6-tri-(N-n-butyl-N'-methylene urea) hexane were substituted for the 1,3,6-tri(N-tert.-butyl-N'-methylene urea) hexane. The infrared spectrum of the clear yellow oil showed a large carbodiimide band (2130 cm$^{-1}$). The polyfunctional carbodiimide solution, which was 90.5% active in hexane, had a Brookfield viscosity of 18.7 cps (lVT #1 spindle at 60 rpm). The yield of the multifunctional carbodiimide was 67.7%. Titration of an aliquot yielded a carbodiimide functionality of 25.0% (theory 28.8%). The theoretical functionality of the material was 3.

EXAMPLE 5

Preparation of 1,3,6-tri(N-cyclohexyl-N'-methylene carbodiimide) hexane

The preparation of the polyfunctional carbodiimide was as described in Example 3 except that 131.72 g (0.2400 mole) of 1,3,6-tri(N-cyclohexyl-N'-methylene urea) hexane. The infrared spectrum of the clear amber oil showed a large carbodiimide band (2130 cm$^{-1}$). The final polyfunctional carbodiimide solution, which was 92.7% active in hexane, had a Brookfield viscosity of 152 cps (LVT #2 spindle at 60 rpm). The yield of the polyfunctional carbodiimide was 43.4%. Titration of an aliquot yielded a carbodiimide functionality of 23.0% (theory 25.5%). The theoretical functionality of the material was 3.

EXAMPLE 6

Preparation of 1,3,6-tri(N-phenyl-N'-methylene carbodiimide) hexane

Into a 3-neck, 2,000 ml, round-bottom flask equipped with a thermometer, mechanical stirrer, and pressure-equalizing dropping funnel were charged 157.47 g (0.6004 mole) of triphenylphosphine and 905 ml of dried methylene chloride. The contents of the flask were cooled to 0° C., then 95.95 g (0.6004 mole) of bromine in 95 ml of methylene chloride were dropped slowly into the stirred triphenylphosphine solution over a 1.4-hour period while maintaining the temperature of the contents of the flask between 0° and 7° C. After the addition of the bromine solution, 122.78 g (1.2134 moles) of triethylamine were added to the bromotriphenylphosphine bromide solution over a 33-minute period while maintaining the temperature of the contents of the flask between 0° and 2° C.

To prepare the polyfunctional carbodiimide, 100.0 g (0.1884 mole) of 1,3,6-tri(N-phenyl-N'-methylene urea) hexane were added portionwise to the stirred solution of bromotriphenylphosphine bromide solution over a 55-minute period while maintaining the temperature of the contents of the flask between 1° and 5° C. After the addition of the urea, the contents of the flask were stirred for 2 hours while maintaining the temperature between −3° and 3° C.

After the reaction period, the triphenylphosphine oxide and triethyl hydrogen bromide were filtered from the polyfunctional carbodiimide solution. The polyfunctional carbodiimide solution was then washed with 1357 g of cold water. The solution containing the multifunctional carbodiimide was then dried overnight over 4 Å molecular sieves.

The methylene chloride was then removed using a roto-evaporator at 38° C. (345 mm Hg). The vacuum was gradually reduced to 3 mm Hg. The 1,3,6-tri(N-phenyl-N'-methylene carbodiimide) hexane was then washed with four 440-ml portions of hexane. The extracts were filtered, then combined to form a clear solution. The hexane was removed with a roto-evaporator at 35° C. (112 mm Hg) until 120 ml of solution remained. The solution was refiltered and most of the remaining hexane removed at 38° C. (9 mm Hg). The infrared spectrum of the clear yellow oil showed a large carbodiimide band (2130 cm$^{-1}$). The multifunctional carbodiimide solution, which was 83.6% active carbodiimide in hexane, had a Brookfield viscosity of 30 cps (LVT #2 spindle at 60 rpm). The yield of carbodiimide was 20.7%. Titration of an aliquot by the procedure of Zarembo and Watts yielded a carbodiimide functionality of 26.5% (theory 26.4%). The theoretical functionality was 3.

EXAMPLE 7

Preparation of 1,3,6-tri(N-isopropyl-N'-methylene thiourea) hexane

Into a 3-neck, 500 ml, round-bottom flask equipped with a condenser, mechanical stirrer, thermometer, and dropping funnel were charged 52.52 g (0.5192 mole) of isopropyl isothiocyanate and 226 ml of methylene chloride. To the stirred methylene chloride solution of isopropyl isothiocyanate were added 30.00 g (0.1731 mole) of 4-aminoethyl-1,8-octanediamine in 22.5 ml of methylene chloride over a 27-minute period. At the end of the feed, the contents of the flask were refluxed at 38° C. for 1 hour. Infrared analysis confirmed the reaction of the isopropyl isothiocyanate with the amine. A band at 1,545 cm$^{-1}$ confirmed the formation of the 1,3,6-tri(N-isopropyl-N'-methylene thiourea) hexane. The product was crystallized from methylene chloride, then vacuum dried overnight at 65° C. The yield of the thiourea was 98.3%.

EXAMPLE 8

Preparation of 1,3,6-tri(N-isopropyl-N'-methylene carbodiimide) hexane

Into a 3-neck, 3,000 ml, round-bottom flask equipped with a thermometer, bubbler, and mechanical stirrer were charged 1762 ml of water and 211 g (5.28 moles) of sodium hydroxide. After cooling the basic water solution to 2° C., 124.89 g (1.7613 moles) of chlorine were bubbled in while maintaining the temperature between 2° and 5° C.

To prepare the polyfunctional carbodiimide, 246 ml of methylene chloride were added to the flask and 69.94 g (0.1467 mole) of 1,3,6-tri(N-isopropyl-N'-methylene thiourea) hexane were added portionwise to the stirred hypochlorite over a 1.7-hour period while maintaining the temperature at 3° C. After the addition of the thiourea, the contents of the flask were stirred for 4 hours at 7° C., then the organic phase was separated from the water layer. The organic phase was filtered to remove residual sulfur. The water phase was washed twice with 50-ml portions of methylene chloride, and the methylene chloride extracts were combined with the organic phase. The organic phase was then dried overnight over 4 Å molecular sieves.

The methylene chloride was then removed using a roto-evaporator at 38° C. (180 mm Hg). The vacuum was gradually reduced over a 2.5-hour period to 12 mm Hg. The infrared spectrum of the amber oil showed a carbodiimide band (2130 cm$^{-1}$). The polyfunctional carbodiimide solution, which was 82.5% active carbodiimide in methylene chloride, had a Brookfield viscosity of 23 cps (LVT #1 spindle at 60 rpm). The yield of carbodiimide was 69.8%. Comparison of its infrared spectrum with that in Example 2 showed that the above preparation yielded a carbodiimide functionality of 29.2% (theory 32.0%). The theoretical functionality of the material was 3.

EXAMPLE 9

Preparation of 1,3,6-tri(N-methyl-N'-methylene thiourea) hexane and Corresponding Carbodiimide The procedure of Example 7 was repeated except that methyl isocyanate was used in place of isopropyl isocyanate to produce 1,3,6-tri(N-methyl-N'-methylene thiourea) hexane. This material was then converted to 1,3,6-tri(N-methyl-N'-methylene carbodiimide) hexane by the procedure of Example 2, except that the tri(methyl thiourea) was used in place of the tri(isopropylurea), on an equal mole basis. The purified product was a very fluid amber liquid, recovered at a yield of approximately 67%. The relatively low yield may have been the result of suspected relatively high solubility in the wash water.

EXAMPLE 10

Preparation of 1,3,6-tri(N-t-butyl-N'-methylene thiourea) hexane

Into a 3-neck, 500 ml, round-bottom flask equipped with a condenser, mechanical stirrer, thermometer, and dropping funnel were charged 59.82 g (0.5192 mole) of tert.-butyl-isothiocyanate and 141.4 ml of methylene chloride. To the stirred methylene chloride solution of tert.-butyl isothiocyanate were added 30.00 g (0.1731 mole) of 4-aminomethyl-1,8-octanediamine in 22.5 ml of methylene chloride over a 30-minute period. The contents of the flask were then refluxed for 23 hours. To the contents of the flask was then added an additional 0.5 g of 4-aminomethyl-1,8-octanediamine, and the contents refluxed for an additional 10 minutes. Theoretical yield of thiourea was 89.8 g.

EXAMPLE 11

Preparation of 1,3,6-tri(N-tert.-butyl-N'-methylene carbodiimide) hexane

Into a 3-neck, 3,000 ml, round-bottom flask equipped with a thermometer, bubbler, and mechanical stirrer were charged 2065 g of water and 247.3 g (6.19 moles) of sodium hydroxide. The basic solution was cooled to 0° C., then 146.39 g (2.0645 moles) of chlorine were bubbled into the basic water solution.

To prepare the polyfunctional carbodiimide, 89.82 g (0.1731 mole) of 1,3,6-tri(N-tert.-butyl-N'-methylene thiourea) hexane in 218 g of methylene chloride were added to the stirred hypochlorite solution over a 3-minute period while maintaining the temperature between −5° and −6° C. After the addition, the reaction was run for 3.3 hours while maintaining the temperature between −5° and 5° C. After the reaction period, the contents of the flask were cooled to −9° C., then the organic phase was separated from the water layer. The organic phase was filtered to remove residual sulfur, washed with 50 ml of water, then dried overnight over 4 Å molecular sieves.

The organic phase was then refiltered, and the methylene chloride removed using a roto-evaporator at 38° C. (345 mm). During the removal of the methylene chloride, the temperature was increased to 50° C. (5 mm) over 3.5 hours. The infrared spectrum of the amber oil showed a large carbodiimide band (2130 cm$^{-1}$). The yield of the carbodiimide, which was 47.9% active carbodiimide in methylene chloride, was 52.2%. Titration of an aliquot by the procedure of Zarembo and Watts yielded a percent carbodiimide functionality of 23.3% (theory 28.8%).

EXAMPLE 12

Preparation of 1,3,6-tri(N-cyclohexyl-N'-methylene thiourea) hexane

Into a 3-neck, 1,000 ml, round-bottom flask equipped with a condenser, mechanical stirrer, thermometer, and dropping funnel were charged 126.61 g (0.8964 mole) of cyclohexylisothiocyanate and 244 ml of methylene chloride. To the stirred methylene chloride solution of cyclohexylisothiocyanate were added 51.78 g (0.2987 mole) of 4-aminomethyl-1,8-octanediamine in 38.9 ml of methylene chloride over 57 minutes. The contents of the flask were refluxed for 3 hours.

Infrared analysis confirmed the reaction of the cyclohexylisothiocyanate with the amine. A band of 1,550 cm$^{-1}$ confirmed the formation of the 1,3,6-tri(N-cyclohexyl-N'-methylene thiourea) hexane. Theoretical yield of thiourea is 178.39 g.

The thiourea in this preparation was not isolated and was used in the preparation of 1,3,6-tri(N-cyclohexyl-N'-methylene carbodiimide) hexane described in Example 13, below.

EXAMPLE 13

Preparation of 1,3,6-tri(N-cyclohexyl-N'-methylene carbodiimide) hexane

Into a 3-neck, 5,000 ml, round-bottom flask equipped with a thermometer, bubbler, and mechanical stirrer were charged 3565 ml of water and 426.99 g (10,676 moles) of sodium hydroxide. The basic water solution was cooled to $-5°$ C., then 257.91 g (3.628 moles) of chlorine were bubbled into the basic water solution while maintaining the temperature between $-3°$ and 31 5° C.

To prepare the multifunctional carbodiimide, 173.92 g (0.2913 mole) of 1,3,6-tri(N-cyclohexyl-N'-methylene thiourea) hexane in 376.55 g of methylene chloride were added to the stirred hypochlorite solution over a 3-minute period. After the addition of the thiourea, the reaction was run for 4 hours while maintaining the temperature between 5° and 8° C. The contents of the reactor were then cooled to $-5°$ C., then the organic phase was separated from the water layer. The organic phase was filtered to remove residual sulfur, washed with 100 ml of water, then dried overnight over 4 Å molecular sieves.

After drying, the organic phase was refiltered, and the methylene chloride was removed using a roto-evaporator at 38° C. (345 nm Hg). During the removal of the methylene chloride, the temperature was gradually increased over a 2-hour period to 50° C. (7 mm Hg). The infrared spectrum of the amber oil showed a large carbodiimide band (2130 cm$^{-1}$). The polyfunctional carbodiimide solution was 90.3% active carbodiimide in hexane. The yield of carbodiimide was 69.1%. Titration of an aliquot by the procedure of Zarembo and Watts yielded a percent carbodiimide functionality of 18.8% (theory 25.5%). The theoretical functionality of the material was 3.

EXAMPLE 14

Preparation of Hexafunctional Carbodiimide

Part A: Preparation of a Tetrafunctional Amine

Into a 3-neck, 500 ml, round-bottom flask equipped with a condenser, mechanical stirrer, thermometer, drop funnel and thermometer were charged 30.00 g (0.1731 mole) of 4-aminomethyl-1,8-octanediamine and 200 ml of methylene chloride. To the stirred methylene chloride solution of amine are added 19.21 g (0.08653 mole) of isophorone diisocyanate at such a rate as to keep the temperature below 38° C. The contents of the flask are refluxed at 38° C. for 1 hour. A monodisperse fraction of tetra-amine with a molecular weight of 569 g/mole is obtained from the crude amine by high-pressure gel permeation chromatography. The theoretical yield of tetra-amine is 49.21 g.

Part B: Preparation of Hexafunctional Urea

To the stirred methylene chloride solution of the tetra-amine (49.21 g) of Example 14, Part A, are added 42.38 g (0.4979 mole) of isopropylisocyanate in 42 ml of methylene chloride. During the addition of the isopropylisocyanate, the temperature is kept below 39° C. After the addition of the isocyanate, the mixture of urea in methylene chloride is stirred for 1 hour at 38° C. The solids are then filtered, washed with methylene chloride, and dried under vacuum at 64° C. overnight. Theoretical yield is 78.7 g.

Part C: Preparation of Hexafunctional Carbodiimide

The preparation of the polyfunctional carbodiimide is as described in Example 3, except that 68.28 g (0.0751 mole) of the hexafunctional urea is substituted for the 1,3,6-tri(N-tert.-butyl-N'-methylene urea) hexane. The theoretical yield of the hexafunctional carbodiimide is 60.2 g.

EXAMPLE 15

Preparation of Tetrafunctional Carbodiimide

Part A: Preparation of Tetrafunctional Thiourea

To the stirred methylene chloride solution of the tetra-amine of Example 14 (49.21 g) are added 70.32 g (0.4979 mole) of cyclohexylisothiocyanate in 42 ml of methylene chloride. During the addition of the cyclohexylisothiocyanate, the temperature is kept below 39° C. After the addition of the isothiocyanate, the solution is stirred for 2 hours at 38° C. The solute is then crystallized and dried under vacuum at 64° C. overnight. Theoretical yield is 98.1 g.

Part B: Preparation of Tetrafunctional Carbodiimide

The preparation of the tetrafunctional carbodiimide is as described in Example 8, except that 98.0 g (0.0864 mole) of the tetrafunctional thiourea are substituted for the 1,3,6-tri(N-isopropyl-N'-methylene thiourea) hexane. The theoretical yield is 86.2 g.

CONTROL 1

Example 1 of U.S. Application Ser. No. 691,378 filed Jan. 15, 1985

Into a 1,000 ml round-bottom flask equipped with heating mantle, mechanical stirrer, thermometer, and nitrogen sparge were charged 68.7 g n-butyl isocyanate, 231.2 g isophorone diisocyanate, 270 g amyl acetate, and 30 g of a 10% solution by weight of 3-methyl-1-phenyl-2-phospholene-1-oxide. The mixture was heated, with stirring at 140° C. for 25.5 hours, then cooled and packaged (533.4 g). The infrared spectrum of the material showed elimination of the isocyanate peak (2260 cm$^{-1}$) with formation of the carbodiimide peak (2130 cm$^{-1}$).

The material was evaluated to have a color rating of 3 (Gardner Hellige Coomparator) and a viscosity of less than 0.5 stoke (Gardner Bubble Viscometer). Titration of an aliquot by the procedure of Zaremko and Watts (*Michrochem. J. Symp. Ser.*, 2, 591, (1962) yielded a percent carbodiimide functionality of 9.78% (theory 10.2%). The theoretical functionality of the material was 4.

The carbodiimide of Control 1 was a polydisperse carbodiimide having n-butyl end groups.

EXAMPLE 16

Evaluations of the Multifunctional Carbodiimides of Examples 2-6 as Crosslinkers in a Coating Prepared from a Carboxylated, Water-Borne Polymer To evaluate the performance of the branched multifunctional carbodiimides of Examples 2-6 as crosslinkers, coatings were prepared based on the following partial formulation:

| | |
|---|---|
| UCAR 4620 (46.33% total solids) | 100.91 g |
| Dimethylethanolamine in water (50%) | 0.40 g |
| Butyl CELLOSOLVE | 7.48 g |
| Water | 7.48 g |

Emulsions of the multifunctional carbodiimides were added to the above partial formulation at 1, 3, and 5 parts of dry carbodiimide resin per 100 parts of dry latex resin (PHR).

To prepare the emulsions, the following typical procedure was used. An oil phase and a water phase were prepared with the following recipes:

| | |
|---|---|
| Oil Phase | |
| 1,3,6-tri(N-cyclohexyl-N'-methylene carbodiimide) hexane | 20.62 g |
| Amyl Acetate | 19.37 g |
| (Oil phase is 47.8% active carbodiimide in amyl acetate) | |
| Water Phase | |
| CELLOSIZE QP-52000 | 0.239 g |
| Triethylamine | 0.638 g |
| TERGITOL NP-40 | 0.451 g |
| AEROSOL-OT (75%) | 0.730 g |
| Water | 29.622 g |

For emulsification, the oil phase is rapidly stirred with a 3-blade impeller, then the water phase is added over a 1 to 2 minute period. After the addition of the water phase, the emulsion is stirred rapidly for 5 minutes. To obtain a smaller droplet size, the emulsion is homogenized with a laboratory scale VirTis homogenizer (90% power for 3 minutes). Analysis gave an average droplet size of 0.83 micron.

The above emulsification procedure is general and was used to make the multicarbodiimides prepared in Examples 2-6 water-dispersible.

For comparison, formulations were prepared in which XAMA-7, a known water-soluble aziridine crosslinker of the prior art, was substituted for the multifunctional carbodiimide emulsions.

Formulations were prepared as described above, then small aliquots placed in Teflon ® molds. After air drying for at least two days, the films were cured at 260° F. for 15 minutes in a forced-air oven at an air velocity of ~400 ft/min. During the curing procedure it is desirable to use an oven air velocity of several hundred ft/min., if possible. This permits rapid removal of water and volatilization of amine, thereby maximizing actual time at cure temperature. Tensile strength, and resistance to swell in methyl ethyl ketone were then determined, as shown in Table I.

TABLE I

| PHR of Cross-linkers | Tensile Strength at Break, psi Examples | | | | | |
|---|---|---|---|---|---|---|
| | 2 | 3 | 4 | 5 | 6 | XAMA-7 |
| 1 | 367 | 323 | 283 | 470 | 297 | 370 |
| 3 | 479 | 990 | 364 | 629 | 629 | 651 |
| 5 | 1425 | 976 | 866 | 888 | 1326 | 867 |

To determine the cured films' resistance to swelling in methyl ethyl ketone, the films were placed in methyl ethyl ketone for at least 2 days. The ratio of the weight of the swollen polymer film to that of the dry polymer film (WSP/WDP) was then determined. These results are shown in Table II.

TABLE II

| PHR of Cross-linkers | WSP/WDP Examples | | | | | |
|---|---|---|---|---|---|---|
| | 2 | 3 | 4 | 5 | 6 | XAMA-7 |
| 1 | 5.192 | 4.087 | 4.192 | 4.722 | 3.987 | 4.116 |
| 3 | 3.054 | 3.169 | 3.100 | 3.131 | 3.450 | 2.976 |
| 5 | 2.965 | 2.940 | 2.778 | 2.725 | 3.061 | 2.804 |

The combination of increased tensile strength and increased resistance to swell in methyl ethyl ketone of the cured films show that crosslinking of the films has occurred and that the amount of crosslinking depends upon the level of crosslinker.

EXAMPLE 17

Reactivity and Efficiency Evaluations of the Multifunctional Carbodiimides Prepared in Examples 2-6 and 9 in a Coating Prepared from a Carboxylated, Water-borne Polymer The reactivity and efficiency of the multifunctional carbodiimides prepared in Examples 2-6 and Control 1 were evaluated using the formulation and emulsification procedure described in Example 16. The emulsification procedure for the product of Example 9 was essentially similar to that described above for Examples 2-6 except that, instead of the Virtis homogenizer, a Heat Systems Ultrasonics, Inc., ultrasonic dispersing device was used (Sonicator Model W-225, Probe Model C2, pulsed mode, 15-20% power for 1-2 minutes). Films from the formulations were cast over Leneta paper, using a No. 60 wire-wound rod, then cured in a forced air oven (air velocity ~400 ft/min). The cured coatings were evaluated by the double-rub test. The results are shown in Table III.

TABLE III

Methyl Ethyl Ketone Double-Rubs

| Curing Cycle | | 1 PHR | | | | | | |
|---|---|---|---|---|---|---|---|---|
| Time (mins) | Temp. (°F.) | Ex. 2 | Ex. 3 | Ex. 4 | Ex. 5 | Ex. 6 | XAMA-7 | Control 1 |
| 15 | 140 | 25 | 20 | 32 | 20 | 39 | 55 | 48 |
| 5 | 185 | 24 | 22 | 22 | 42 | 24 | — | 28 |
| 5 | 200 | — | 30 | 21 | 32 | 63 | — | — |
| 15 | 260 | 40 | 43 | 28 | 88 | +300 | 255 | 45 |

| Curing Cycle | | 2 PHR | | | | | | |
|---|---|---|---|---|---|---|---|---|
| Time (mins) | Temp. (°F.) | Ex. 2 | Ex. 3 | Ex. 4 | Ex. 5 | Ex. 6 | XAMA-7 | Control 1 |
| 15 | 140 | 40 | 34 | 95 | 68 | 55 | 37 | 43 |
| 5 | 185 | 75 | 42 | 103 | 70 | 67 | 56 | 45 |
| 5 | 200 | — | 88 | 131 | 97 | 60 | — | — |
| 15 | 260 | 157 | +300 | +300 | +300 | +300 | +300 | +300 |

| Curing Cycle | | 3 PHR | | | | | | | |
|---|---|---|---|---|---|---|---|---|---|
| Time (mins) | Temp. (°F.) | Ex. 2 | Ex. 3 | Ex. 4 | Ex. 5 | Ex. 6 | Ex. 9 | XAMA-7 | Control 1 |
| 15 | 140 | 93 | 42 | 140 | 89 | 82 | — | 50 | 94 |
| 30 | 140 | — | — | — | — | — | +300 | — | — |
| 5 | 185 | 140 | 54 | +300 | +300 | 70 | +300 | 73 | 86 |
| 5 | 200 | — | 90 | +300 | +300 | 121 | — | 225 | 112 |
| 15 | 260 | +300 | +300 | +300 | +300 | +300 | — | +300 | 300 |
| 18 hrs | Room | — | — | — | — | — | +300 | — | — |

| Curing Cycle | | 4 PHR | | | | | | |
|---|---|---|---|---|---|---|---|---|
| Time (mins) | Temp. (°F.) | Ex. 2 | Ex. 3 | Ex. 4 | Ex. 5 | Ex. 6 | XAMA-7 | Control 1 |
| 15 | 140 | 86 | 42 | 94 | 125 | 79 | 48 | 55 |
| 5 | 185 | 164 | 72 | +300 | 235 | 126 | 80 | 73 |
| 5 | 200 | 300 | 74 | +300 | +300 | 280 | 300 | 106 |
| 15 | 260 | +300 | +300 | +300 | +300 | +300 | +300 | +300 |

The tabulated results, particularly the results of Table III wherein the carbodiimides were used in amounts of 3-4PHR, show that carbodiimides having isopropyl, n-butyl, cyclohexyl, phenyl or methyl end groups have significantly faster "cure speeds" at relatively low temperatures, on the order of 140° C.-185° C. (Examples 2, 4, 5, 6 and 9, respectively) than a carbodiimide having t-butyl end groups (Example 3) or a polydisperse carbodiimide prepared as described in Example 1 of U.S. application Ser. No. 691,378 filed Jan. 15, 1985 (Control 1).

EXAMPLE 18

Evaluation of 1,3,6-tri(N-cyclohexyl-N'-methylene carbodiimide) hexane from Example 13

The trifunctional carbodiimide prepared in Example 13 was emulsified using the procedure described in Example 16. Using the formulation below, cured films were cast as described above, then evaluated for resistance to methyl ethyl ketone double-rubs.

| Formulation | |
|---|---|
| UCAR 4620 (46.33% solids) | 100.81 g |
| Dimethylethanolamine in water (50%) | 0.40 g |
| Butyl CELLOSOLVE | 2.48 g |
| Water | 7.48 g |
| Emulsion of Example 16 (26.68% active) | 5.26 g (3 PHR) |

Films of the above formulation were cast over Leneta paper, then cured in a forced air oven under the conditions described in Table IV. The cured coatings were evaluated by methyl ethyl ketone double-rubs.

TABLE IV

Methyl ethyl Ketone Double-Rubs

| Curing Cycle | | |
|---|---|---|
| Time (minutes) | Temperature (°F.) | Methyl ethyl Ketone Double-Rubs |
| 2 | 140 | 48 |
| 15 | 140 | 71 |
| 5 | 185 | 79 |
| 5 | 200 | 169 |
| 15 | 260 | +300 |

The results above show that the polyfunctional carbodiimide prepared in Example 13 is capable of producing crosslinked films.

EXAMPLE 19

Evaluation of 1,3,6-tri(N-cyclohexyl-N'-methylene carbodiimide) hexane from Example 5

The multifunctional carbodiimide prepared in Example 5 was emulsified using the procedure described in Example 16. Using the formulation below, cured films were prepared, then evaluated for resistance to methyl ethyl ketone double-rubs.

| Formulation | |
|---|---|
| UCAR 4431 (42.2% solids) | 55.86 g |
| Dimethylethanolamine in water (50%) | 0.30 g |
| Butyl CELLOSOLVE | 3.74 g |
| Water | 3.74 g |
| Emulsion of Example 5 (26.68% active) | 2.63 g (3 PHR) |

Films of the above formulation were cast over Leneta paper, then cured in a forced air oven under the conditions described in Table V. The cured coatings were evaluated by methyl ethyl ketone double-rubs.

TABLE V

| Methyl ethyl Ketone Double-Rubs | | |
|---|---|---|
| Curing Cycle | | |
| Time (minutes) | Temperature (°F.) | Methyl ethyl Ketone Double-Rubs |
| 2 | 140 | 100 |
| 15 | 140 | +300 |
| 5 | 185 | +300 |
| 5 | 200 | +300 |

It is known that carbodiimides tend to dimerize and/or trimerize at temperatures as low as room temperature, which could lead to instability of carbodiimide compounds or compositions made from them. The rate of dimerization and/or trimerization will be affected by the nature of the terminal group attached to each carbodiimide group. With reference to the compounds made in Examples 2-6, these terminal groups are as follows:

| Example | Terminal Group | Mol. Wt. |
|---|---|---|
| 2 | $(CH_3)_2CH-$ | 374.6 |
| 4 | $CH_3(CH_2)_3-$ | 416.7 |
| 3 | $(CH_3)_3C-$ | 416.7 |
| 6 | $C_6H_5-$ | 476.7 |
| 5 | $C_6H_{11}-$ | 494.8 |

EXAMPLE 20

Stability of Polyfunctional Carbodiimide Solutions

To demonstrate the effect of the terminal groups, the stability of solutions of the trifunctional carbodiimides of Examples 2-6 was evaluated at 25° C. and 50° C. During the evaluation period, the solutions were visually inspected each day until a no-flow material was obtained which was insoluble in amyl acetate. Results are shown in the first and second columns of Table VI.

TABLE VI

| | Time to Gel (Days) | | |
|---|---|---|---|
| Compound | (at 50° C.) 93% Active in Hexane | (at 25° C.) 93% Active in Hexane | (at 50° C.) 46% Active in Amylacetate |
| 1,3,6-tri(N-isopropyl-N'-methylene carbodiimide) hexane | 28 | 200 | 34 |
| 1,3,6-tri(N-n-butyl-N'-methylene carbodiimide hexane | 4 | 48 | 6 |
| 1,3,6-tri(N-t-butyl-N'-methylene carbodiimide hexane | 87 | 200 | 87 |
| 1,3,6-tri(N-phenyl-N'-methylene carbodiimide) hexane | 13[a] | 151[a] | 22[b] |
| 1,3,6-tri(N-cyclohexyl-N'-methylene carbodiimide) hexane | 41 | 180 | 66 |

[a]The trifunctional carbodiimide was 83% active in hexane.
[b]The trifunctional carbodiimide was 41% active in amyl acetate.

With reference to Table VI, the stability effect may be depicted as follows:

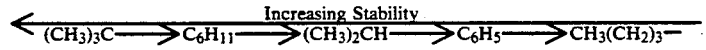

The effect of dilution on the stability of the trifunctional carbodiimides is illustrated by the third column of Table VI. It will be observed that dilution significantly improves heat stability, as would be expected since the reaction rate between carbodiimide moieties is presumably concentration-dependent, according to standard kinetic theory.

What is claimed is:

1. A branched, monodisperse, multifunctional carbodiimide having methyl, isopropyl, n-butyl, cyclohexyl or phenyl end groups, said carbodiimide providing improved low temperature curing characteristics for cross-linkable compositions containing a carboxyl-containing emulsion resin or a neutralized, carboxylated water-soluble organic resin when said carbodiimide is present in an amount of at least about 3 parts per 100 parts resin.

2. A branched, monodisperse, multifunctional carbodiimide as defined in claim 1 having methyl end groups.

3. A branched, monodisperse, multifunctional carbodiimide as defined in claim 1 having isopropyl end groups.

4. A branched, monodisperse, multifunctional carbodiimide as defined in claim 1 having n-butyl end groups.

5. A branched, monodisperse, multifunctional carbodiimide as defined in claim 1 having cyclohexyl end groups.

6. A branched, monodisperse, multifunctional carbodiimide as defined in claim 1 having phenyl end groups.

7. The carbodiimide, 1,3,6-tri(N-methyl-N'-methylene carbodiimide) hexane as defined in claim 1.

8. The carbodiimide, 1,3,6-tri(N-isopropyl-N'-methylene carbodiimide) hexane as defined in claim 1.

9. The carbodiimide, 1,3,6-tri(N-n-butyl-N'-methylene carbodiimide) hexane as defined in claim 1.

10. The carbodiimide, 1,3,6-tri(N-cyclohexyl-N'-methylene carbodiimide) hexane as defined in claim 1.

11. The carbodiimide, 1,3,6-tri(N-phenyl-N'-methylene carbodiimide) hexane as defined in claim 1.

12. An aqueous emulsion of a carbodiimide as defined in claim 1.

13. A cross-linkable composition comprising a mixture of a carboxyl-containing emulsion resin or neutralized, carboxylated water-soluble organic resin and a branched, monodisperse, multifunctional carbodiimide having methyl, isopropyl, n-butyl, cyclohexyl or phenyl end groups, said carbodiimide being present in an amount of at least about 3 parts per hundred parts resin.

14. A cross-linkable composition as defined in claim 13 wherein said carbodiimide is a branched, monodisperse, multifunctional carbodiimide having methyl end groups.

15. A cross-linkable composition as defined in claim 13 wherein said carbodiimide is a branched, monodisperse, multifunctional carbodiimide having isopropyl end groups.

16. A cross-linkable composition as defined in claim 13 wherein said carbodiimide is a branched, monodisperse, multifunctional carbodiimide having n-butyl end groups.

17. A cross-linkable composition as defined in claim 13 wherein said carbodiimide is a branched, monodisperse, multifunctional carbodiimide having cyclohexyl end groups.

18. A cross-linkable composition as defined in claim 13 wherein said carbodiimide is a branched, monodisperse, multifunctional carbodiimide having phenyl end groups.

19. A cross-linkable composition as defined in claim 13 wherein said carbodiimide is 1,3,6-tri(N-methyl-N'-methylene carbodiimide) hexane.

20. A cross-linkable composition as defined in claim 13 wherein said carbodiimide is 1,3,6-tri(N-isopropyl-N'-methylene carbodiimide) hexane.

21. A cross-linkable composition as defined in claim 13 wherein said carbodiimide is 1,3,6-tri(N-n-butyl-N'-methylene carbodiimide) hexane.

22. A cross-linkable composition as defined in claim 13 wherein said carbodiimide is 1,3,6-tri(N-cyclohexyl-N'-methylene carbodiimide) hexane.

23. A cross-linkable composition as defined in claim 13 wherein said carbodiimide is 1,3,6-tri(N-phenyl-N'-methylene carbodiimide) hexane.

24. The cross-linked product of the cross-linkable composition defined in claim 13.

* * * * *